United States Patent
Sevastianov

(10) Patent No.: US 7,273,466 B2
(45) Date of Patent: Sep. 25, 2007

(54) APPARATUS HAVING A DEFOAMER-COATED SURFACE AND USE OF A DEFOAMER-CONTAINING SURFACE

(75) Inventor: Viktor I. Sevastianov, Moskau (RU)

(73) Assignee: Jostra AG, Hirrlingen (DE)

( * ) Notice: Subject to any disclaimer, the term of this patent is extended or adjusted under 35 U.S.C. 154(b) by 423 days.

(21) Appl. No.: 10/191,699

(22) Filed: Jul. 9, 2002

(65) Prior Publication Data

US 2003/0026730 A1  Feb. 6, 2003

(30) Foreign Application Priority Data

Jul. 13, 2001 (DE) .................... 101 35 277

(51) Int. Cl.
*A61M 5/00* (2006.01)
*A61M 1/00* (2006.01)

(52) U.S. Cl. ............................ 604/8; 422/44

(58) Field of Classification Search ............ 604/4.01, 604/6.01, 6.14, 6.15, 403, 405, 406, 415, 604/903; 422/44–48; 210/646, 321.81, 210/321.9, 500.23, 500.24; 128/DIG. 3; 261/DIG. 28; 55/16, 158
See application file for complete search history.

(56) References Cited

U.S. PATENT DOCUMENTS 4,597,894 A * 7/1986 Abe et al. .................. 516/118
5,543,082 A * 8/1996 McGee et al. .............. 516/118
5,582,794 A 12/1996 Hagiwara et al.
6,254,825 B1 * 7/2001 Friedman ...................... 422/44
6,506,340 B1 * 1/2003 Tsai et al. ...................... 422/45

FOREIGN PATENT DOCUMENTS

| EP | 0 630 656 A1 | 12/1994 |
| EP | 0 774 285 A2 | 5/1997 |
| JP | 01067184 A | 3/1989 |
| WO | WO 95/28184 | 10/1995 |

OTHER PUBLICATIONS

Matsuhashi, Toshio, MD et al. In Vivo Evaluation of a Fluorine-Acryl-Styrene-Urethane-Silicone Antithrombogenic Coating Material Copolymer for Intravascular Stents. Acad. Radiol 1996:3:581-588.*

Toshio Matsuhashi et al., In Vivo Evaluation Of A Fluorine-Acryl-Stylene-Urethane-Silicone Antithrombogenic Coating Material Copolymer For Intravascular Stents, 1996; pp. 581-588.

* cited by examiner

*Primary Examiner*—Tatyana Zalukaeva
*Assistant Examiner*—Melanie J Hand
(74) *Attorney, Agent, or Firm*—Harness, Dickey & Pierce, P.L.C.

(57) ABSTRACT

An apparatus for defoaming blood is described, having a surface which comes into contact with blood, said surface being coated with a defoamer which has a hydrophobic component with lipophobic microdomains.

12 Claims, 1 Drawing Sheet

APPARATUS HAVING A DEFOAMER-COATED SURFACE AND USE OF A DEFOAMER-CONTAINING SURFACE

BACKGROUND OF THE INVENTION

1. Field of the Invention

The invention relates to an apparatus for defoaming blood, having a surface which comes into contact with blood and which is coated with a defoamer, and to such a defoamer.

The invention furthermore relates to a use of a surface coming into contact with blood for defoaming blood in an extracorporeal circulation.

2. Related Prior Art

An apparatus of the abovementioned type is disclosed in EP 0 774 285.

Such apparatuses are used for defoaming blood, for example during heart surgery. In open-heart surgery, a heart-lung machine takes over the functions of the patient's heart and lung in an extracorporeal circulation with the aid of pumps and oxygenators. During this, blood, in particular blood aspirated from a surgical wound, is often mixed with air with the formation of foam. This foam or foam bubbles must be removed from the blood before it is reintroduced into the patient who otherwise is exposed to the risk of embolisms.

Thus, for example, an extracorporeal system comprising an oxygenator, blood reservoirs and cardiotomy reservoirs and also blood tubing and filters etc. is expected not only to supply oxygen to and remove $CO_2$ from the blood but also to remove completely the foam caused by the formation of bubbles. Blood filters and other apparatuses such as, for example, bubble traps, separating cyclones and the like, which are integrated into an extracorporeal circulation, cannot replace the use of defoamers in the blood reservoir and especially in the cardiotomy reservoir.

Defoaming is normally achieved by contacting the blood with a very large hydrophobic surface which is coated with a defoaming agent. In particular, open-celled polyurethane foams or textile materials, for example polyester materials, are used as a surface here.

The surfaces are coated with compounds which form a continuous film at the liquid/gas interface and thereby make it possible for the liquid to be degassed to form the smallest surface area. This "defoamer" destroys the gas bubbles.

The by far most frequently used defoamer for coating surfaces coming into contact with blood is silicone oil (polydimethyl-siloxane) or a mixture of polydimethyl-siloxane and silicone dioxide which is marketed by Dow Corning under the trade names "Simethicon®" and "Antifoam A®".

These defoamers have the disadvantage of being slowly washed off from the surface by the streaming blood, thus reducing their effectiveness. As a result, after a while the blood is no longer defoamed sufficiently. The gas bubbles which have not been removed from the blood may cause embolisms in the patient. Moreover, the washing out means that during protracted surgical procedures silicone oil and silica particles may enter the patient and likewise cause embolisms there. This risk is furthermore increased by the fact that presently materials which mainly have improved hemocompatibility are used for the extracorporeal circulation. These then have, for example due to heparinization, a hydrophilic surface so that washed-off silicone oil cannot be trapped anymore by hydrophobic interactions of hydrophobic surfaces in the extracorporeal circulation, before entering the patient.

EP 0 774 285, mentioned at the outset, discloses coating of a hydrophobic surface with a defoamer which contains a triglyceride with at least one fatty acid comprising from 14 to 24 carbon atoms. It is preferred to use castor oil here. The defoamer may also contain a hydrophobic component, for example a silicone compound.

However, this defoamer proved to be much less effective than, for example, Simethicon®.

Moreover, it turned out that in the case of a castor oil-containing defoamer, too, as in the case of surfaces coated only with silicone, the oil is, after protracted use of said defoamer, washed off by the streaming blood, enters the patient and may cause a fat embolism there.

WO 95/28184 discloses a coating of polymers or metals, which has triblock copolymers of polylactone-polysiloxane-polylactone, the siloxane being dimethylsiloxane and the lactone being caprolactone. This coating proved to be particularly biocompatible and suitable for use in extracorporeal circulations, since, in this case, the blood comes into contact with a particularly large surface. Said coating may be applied in a stable manner not only to porous membranes but also to metal surfaces, whereby they became biocompatible.

However, the coating with triblock copolymers proved ineffective when used as defoamer.

SUMMARY OF THE INVENTION

In view of the above, one object underlying the present invention is to provide an apparatus of the type mentioned at the outset, which is coated with a defoamer which is permanent and whose effectiveness, at the same time, is not being reduced with time.

According to the invention, this object is achieved by the fact that the defoamer is composed of a hydrophobic component with lipophilic microdomains.

The invention relates as a further object to a method for defoaming blood comprising the step of contacting blood in an extracorporeal circulation with an apparatus according to the invention.

It is preferred if the hydrophobic component of the coating according to the invention is a silicone compound.

Silicone compounds have proved themselves as coating material for a surface coming into contact with blood and are distinguished by a very high biocompatibility. In this connection, silicone copolymers which have a dimethylsiloxane component having a molecular weight of approx. 1800 to 2600 Da have proved particularly suitable.

In the apparatus according to the invention, an object is achieved if the microdomains contain fluorine and, further, if the defoamer is prepared by a reaction of a silicone compound with a fluorinated dicarboxylic acid or with a fluorinated dicarboxylic acid derivative.

In this connection, it is preferred if the fluorinated dicarboxylic acid derivative is tetrafluoro diethyl succinate.

In fact, the inventor has found that, surprisingly, lipophobic microdomains are formed in a fluorine-containing hydrophobic coating. The air bubbles in the blood are bound via these lipophobic sites and the blood is defoamed in connection with the hydrophobic component. The formation of lipophobic microdomains, in particular, results in good biocompatibility.

Although a coating with fluorine-containing silicone proved to be quite antithrombogenic and biocompatible during usage in intravascular stents (T. Matsuhashi et al.: In vivo Evaluation of a Fluorine-Acryl-Stylene-Urethane-Silicone Antithrombogenic Coating Material Copolymer for Intravascular Stents; Acad. Radiol. 1996; 3: 581-588), the coating composition used therein showed no defoaming action. This, however, is also not expected for the application described there.

In this connection, the surface to be coated with the defoamer according to the invention is selected from the group consisting of hydrophobic materials such as polyurethane, polyesters and other polymers.

Open-celled polyurethane foams have proved themselves in apparatuses for open-heart surgery and are used most frequently in extracorporeal circulations.

In this connection, it cannot be ruled out that other materials, too, can be coated with the defoamer according to the invention.

A further object of the invention relates to the apparatus according to the invention being designed as a filter which can be integrated into an extracorporeal circulation.

Another object of the invention relates to the apparatus with the surface coated according to the invention being designed as defoaming filter in a blood reservoir.

Blood reservoirs which may be used are soft bag reservoirs and/or hard shell reservoirs of common shape.

A further object of the invention relates to a method for defoaming blood comprising the step of contacting blood in an extracorporeal circulation with the apparatus comprising a defoamer according to the invention.

Furthermore, the invention relates as a further object to a defoamer made of a hydrophobic component with lipophobic microdomains.

In fact, it has been found by the inventor that using hydrophobic-lipophobic materials as coating agents can attain a defoaming action comparable to that of Simethicon® and, at the same time, can increase the durability and blood compatibility of the coating.

In the light of this, yet a further object of the invention relates to a defoamer of the general formula

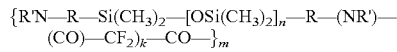

wherein

R is an alkylene or aralkylene group, n is from 5 to 40, preferably 10 to 35,

R' is hydrogen, an alkyl or aralkyl group, k is from 2 to 5 and m is an integer between 1 and 15.

Another object of the invention is related to a method for providing a surface with defoaming properties comprising the step of coating said surface with a defoamer according to the invention.

Further advantages will be evident from the description, the drawing and the examples.

It will be understood that the aforementioned features and the features still to be explained below can be used not only in the combination specified in each case but also in other combinations or on their own, without leaving the scope of the present invention.

BRIEF DESCRIPTION OF THE DRAWINGS

In the figures.

DETAILED DESCRIPTION OF PREFERRED EMBODIMENTS

Figure 1:
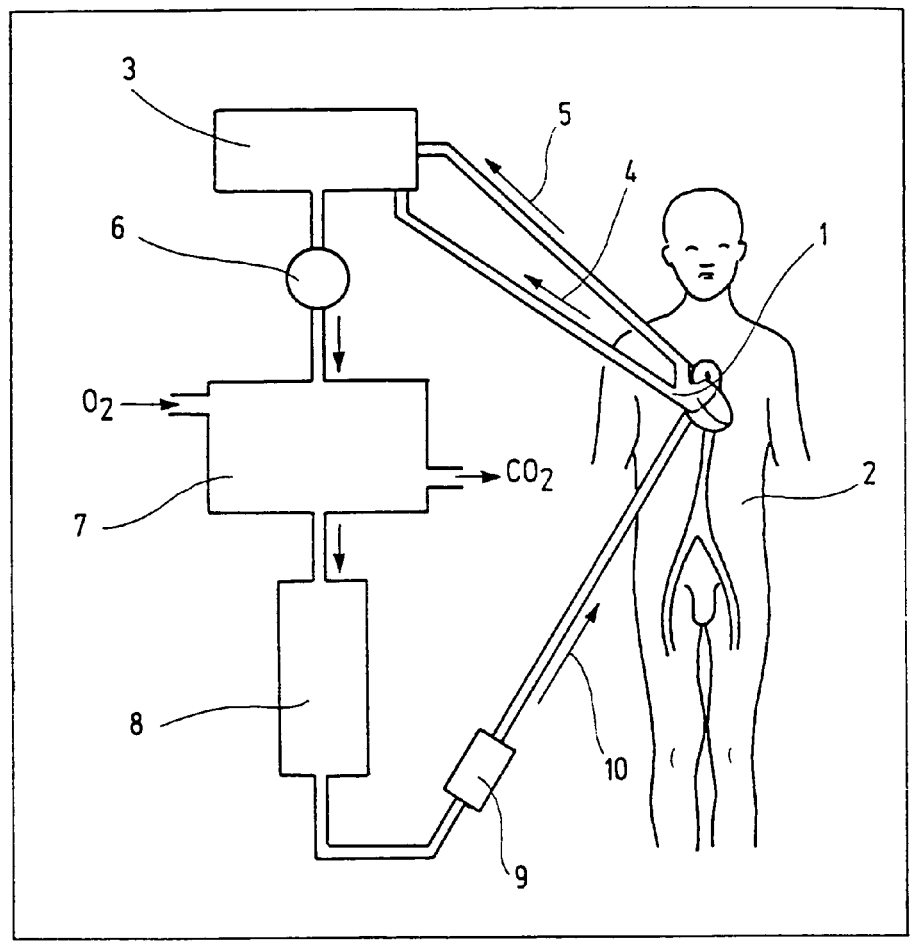
FIG. 1 shows a schematic representation of an extracorporeal circulation in the form of a heart-lung machine.

FIG. 1 shows a heart-lung machine as diagram of an extracorporeal circulation. The heart-lung machine temporarily takes over the pumping function of the heart and the gas exchange function of the lungs.

A tubing system 1 connects the patient's right atrium 2 to the heart-lung machine. Venous blood flows into a blood reservoir 3 that is indicated by the arrow 4. There it is combined with blood which is aspirated via tubes from a surgical wound, which is shown by the arrow 5. The blood reservoir is provided with a defoamer-coated surface.

The mixed blood is transported via a pump 6 into a gas exchanger (oxygenator) 7 in which oxygen is added to and $CO_2$ is removed from the blood. After the blood has been oxygenated, it is led over a heat exchanger 8 which can cool or heat the blood, and thus the patient, to particular temperatures. The heat exchanger 8 is normally an integral component of the oxygenator. Via a filter 9, "arterialized" blood is reintroduced into the patient 2, which is indicated by the arrow 10.

However, in addition to this it is also possible to provide other components which are already present in or can be integrated into an extracorporeal circulation with the coating according to the invention. Thus, the oxygenator or, for example, the filter may be coated such that they have not only their particular original function, i.e. supplying oxygen or trapping blood clots or the like, but also, at the same time, a defoaming action. A precondition for this additional function is a possibility for the collected air to be removed.

Figure 2:
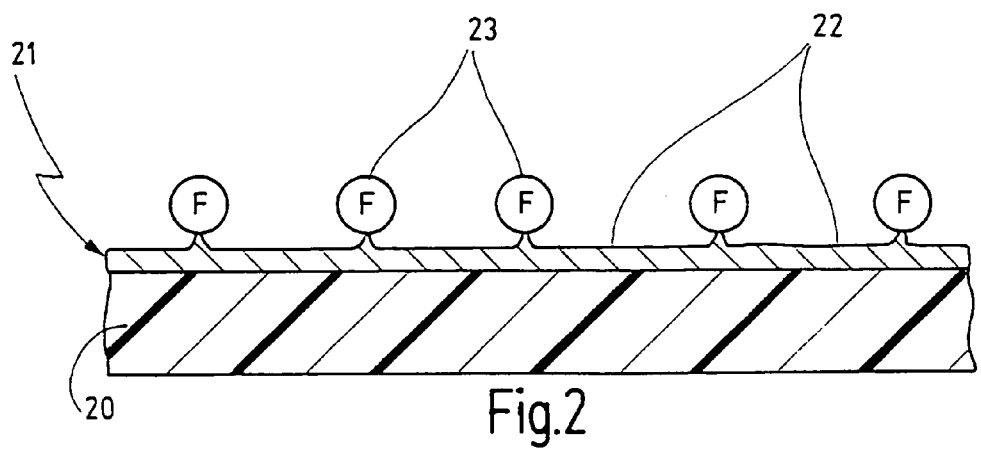
FIG. 2 shows a highly magnified, schematic section of a surface coated according to the invention.

FIG. 2 shows schematically a highly magnified section of a surface coated according to the invention. In this connection, 20 denotes a surface to which a defoamer 21 has been applied. This defoamer 21 has hydrophobic domains 22 and lipophobic microdomains 23 formed by a fluorine-containing component. A suitable fluorine-containing component is, for example, a fluorine-containing carboxylic acid, with the fluorine contained therein forming lipophobic microdomains within a hydrophobic layer formed by a silicone compound.

Examples of a coating according to the invention and the preparation thereof are illustrated in detail below.

EXAMPLES

A) Synthesis of Tetrafluoro Diethyl Succinate

Tetrafluoro diethyl succinate was obtained by reacting tetrafluoro succinic acid with an excess of ethanol in the presence of sulfuric acid as esterification catalyst at 60-75° C. After completion of the reaction, the final product tetrafluoro diethyl succinate (TFDES) is isolated by distillation at 185° C.

B) Synthesis of the Defoamer

In order to prepare the defoamer, 5.2 g ($2 \times 10^{-3}$ mol) of Tegomer A-Si2322 (Goldschmidt AG, Germany), a silicone oligomer with terminal secondary amino groups and a molecular weight of 2600 Da, in 7 ml of isopropanol were introduced into a flask equipped with a magnetic stirrer and a thermometer and protected against humidity by a reservoir. 0.55 g ($2.2 \times 10^{-3}$ mol) tetrafluoro diethyl succinate (TFDES from A) in 4.5 ml of isopropanol was added dropwise and with stirring for 5 min at 20° C. The temperature of the reacting solution was increased in steps: 20° C. for 0.5 h; 40° C. for 1 h; 60° C. for 0.5 h and 75° C. for 0.5 h. After completion of the reaction, the flask was cooled. The resulting solution was kept at 5° C. with no humidity and used without additional purification steps.

C) Coating Procedure

The working solution contained 0.75 to 1% by weight of the substance prepared under B), 95 ml of isopropanol and 5 ml of Novec® HFE7100 (3M, Germany). Samples of polyurethane foams were incubated with the working solution at room temperature for 10 min. After incubation, the samples were completely dried at 50±5° C. for 1 to 2 h and then sterilized by ethylene oxide.

D) Efficiency of the Coating

The efficiency was compared by introducing air into a 10% strength solution of human albumin with stirring and recirculating the resulting foam solution via coated polyurethane foams prepared according to C. At the beginning of the experiment, the defoaming action of polyurethane foams coated only with Simethicon® and of polyurethane foams coated according to the invention was identical, but in the case of samples coated only with Simethicon®, the defoaming action strongly decreased over the course of 20-30 min. The effectiveness of the samples coated according to the invention remained constant over hours.

E) Hydrophobicity and Biological Properties of the Coated Foams

The hydrophobicity of the coated foams from C was assayed by incubating them in distilled water without any air bubbles for 1 h. The samples were then dropped from a level of 2 m on the bases. Then the weight of the samples was measured. The water uptake value was defined as the ratio of the sample weight with water to the weight of the dry sample (g $H_2O$/g dry foam). In order to determine the coating stability, the water uptake value was also measured, after incubating the samples in distilled water for 20 h.

The table below shows a summary of the results of these assays.

| Water uptake (g $H_2O$/g PU foam) | Uncoated PU foam | Simethicon ®-coated | Coated according to the invention |
|---|---|---|---|
| After 1 h | 8.1 ± 1.0 | 5.6 ± 0.8 | 4.3 ± 0.5 |
| After 24 h | Not determined | 7.2 ± 0.9 | 4.6 ± 0.5 |

*PU foam = polyurethane foam

It turned out that the polyurethane foams coated according to the invention are distinctly more hydrophobic than those coated with Simethicon®. This was indicated particularly impressively by the value after 24 h: the hydrophobicity of the foams coated with Simethicon® decreased markedly, i.e. they took up distinctly more water (5.6 g after 1 h, compared with 7.2 g after 24 h, per g of polyurethane foam). In contrast, the water uptake value for the foams coated according to the invention remained virtually constant (4.3 g after 1 h, compared with 4.6 g after 24 h, per g of polyurethane foam).

The hemocompatibility of the coatings was studied on the basis of hemolysis, the plasma recalcification time, the adsorption of $^{131}$iodine-labeled human serum albumin, the appearance of adhering platelets and complement activation.

Hemolysis was assayed by preparing an extract of the coating material in physiological saline and incubating it with blood at 37° C. for 1 h. The coating material was removed and the blood was centrifuged at 400×g for 15 min. The cell-free supernatant was carefully removed; the degree of hemolysis of samples was measured by spectrophotometric measurement at a wavelength of λ=530 to 550 nm.

The plasma recalcification time was determined by incubating the coated polyurethane foams prepared under C with citrate-containing human plasma at 37° C. for 20 min. Subsequently, 0.025 M calcium chloride was added to the plasma. The plasma recalcification time was determined at 37° C. on the basis of the "Fibrintimer II" (Behring, Germany). In this case, plasma which had not been incubated served as a control.

Adsorption of $^{131}$iodine-labeled human serum albumin to the inner surface of the samples was measured using a Copra-5005 gamma counter (Canberra-Packard, USA). The total activity of $^{131}$iodine-labeled human serum albumin (I-HSA) in phosphate-buffered saline (PBS) was no less than 100 cpm/mg min at a total volume concentration of HSA of 30 mg/ml. After incubating in I-HSA-PBS at room temperature for 2 h, the samples were washed in physiological saline with pH 7.4, and then radioactivity was measured in a gamma counter.

The number of adhering thrombocytes was checked by incubating the samples with thrombocyte-enriched plasma and then studying the samples microscopically, in each sample randomly selecting 400 μm².

The total number of thrombocytes was divided into three classes: individual cells, deformed cells and aggregates of two or more cells. This classification reflects thrombocyte activation: the lower the value of thrombocyte adhesion, the higher the probability of biocompatibility of the material assayed.

Complement activation before and after incubating human plasma with the coating materials according to the invention was determined on the basis of the photocolorimetric method. The concentration of hemoglobin released from complement lysed antibody-coated sheep erythrocytes represents complement activity in the serum sample.

The hydrophobicity assay and the stability of the coating materials and the determination of the biological properties are summarized in the table below.

| | Control plasma or serum | Uncoated PU foam | Silicone-coated | Coated according to the invention |
|---|---|---|---|---|
| Hemolysis (%) | — | 0 | 0 | 0 |
| Plasma calcification time (s) | 294 ± 23 | 225 ± 25 | 250 ± 12 | 290 ± 15 |
| $^{131}$I-HSA adsorption (μg/g) | — | 11.6 ± 2.3 | 6.8 ± 1.2 | 13.4 ± 2.6 |
| Thrombocytes (REM) | — | — | Individual cells | Individual cells |
| Complement activation CH50 (%) | 95 ± 5 | — | 35 ± 2 | 50 ± 3 |

Hemolysis was caused neither by uncoated nor coated foams. The table shows that the polyurethane foams coated according to the invention practically did not activate the blood coagulation system, i.e. the time in which the blood coagulates is for these samples virtually identical to the time in which blood coagulates, which was not contacted with foams. In comparison, silicone-coated foams exhibited a distinctly faster activation of the blood coagulation system ("plasma recalcification time"): 250±12 s compared to 294±23 s for untreated plasma.

Furthermore, the complement system was distinctly less activated by the polyurethane foams coated according to the invention than by the silicone-coated foams. Nevertheless, they do not differ from the latter with respect to platelet adhesion.

The polyurethane foams coated according to the invention adsorbed twice the amount of albumin adsorbed by silicone-coated polyurethane foams (13.4±2.6 µg/g compared to 6.8±1.2 µg/g) and practically adsorbed the same amount of albumin as an uncoated foam (11.6±2.3 µg/g).

I claim:

1. An apparatus for defoaming blood, the apparatus having a surface, coated with a defoamer, which comes into contact with blood, wherein said defoamer is composed of a compound having (1) a hydrophobic silicone component and (2) lipophobic microdomains that contain fluorine, wherein the compound is a fluorinated dicarboxylic acid derivative.

2. The apparatus according to claim 1, wherein the defoamer is prepared by reacting a silicone compound with a fluorinated dicarboxylic acid or with a fluorinated dicarboxylic acid derivative.

3. The apparatus according to claim 2, wherein the fluorinated dicarboxylic acid derivative is tetrafluoro diethyl succinate.

4. The apparatus according to claim 1, wherein said defoamer is composed of a compound having a general formula comprising:

$$\{R'N-R-Si(CH_3)_2-[OSi(CH_3)_2]_n-R-(NR')-(CO)-(CF_2)_k-CO-\}_m$$

wherein
R is an alkylene or aralkylene group,
n is from 5 to 40, preferably 10 to 35,
R' is hydrogen, an alkyl or aralkyl group,
k is from 2 to 5 and
m is an integer between 1 and 15.

5. The apparatus according to claim 1, wherein the surface to be coated with the defoamer comprises hydrophobic materials which are selected from the group consisting of polyurethane, polyesters and other polymers.

6. The apparatus according to claim 1, which is designed as a filter which can be integrated into an extracorporeal circulation.

7. The apparatus according to claim 1, which is designed as defoaming filter in a blood reservoir.

8. A method for defoaming blood comprising the step of contacting blood in an extracorporeal circulation with the apparatus of claim 1.

9. A method for defoaming blood comprising the step of contacting blood in an extracorporeal circulation with the apparatus of claim 4.

10. An apparatus for defoaming blood, having a surface, coated with a defoamer, which comes into contact with blood, wherein said defoamer is composed of a compound having a general formula comprising:

$$\{(Silicone)\text{-}(Amide)\text{-}(Lipophobic\ Microdomain)\}_m$$

wherein
the Silicone is hydrophobic,
the Lipophobic Microdomain contains fluorine, and
m is an integer between 1 and 15.

11. The apparatus according to claim 10, wherein said defoamer is composed of a compound having the general formula:

$$R'-\{(NR')\text{-}(Silicone)\text{-}(NR')-(CO)\text{-}(Lipophobic\ Microdomain)\text{-}CO-\}_mOR'$$

wherein
the Silicone is hydrophobic,
the Lipophobic Microdomain contains fluorine,
R' is hydrogen, an alkyl or aralkyl group, and
m is an integer between 1 and 15.

12. The apparatus according to claim 4, wherein said defoamer is composed of a compound having the general formula:

$$R'-\{(NR')-R-Si(CH_3)_2-[OSi(CH_3)_2]_n-R-(NR')-(CO)-(CF_2)_k-CO-\}_mOR'$$

wherein
R is an alkylene or aralkylene group,
n is from 5 to 40, preferably 10 to 35,
R' is hydrogen, an alkyl or aralkyl group,
k is from 2 to 5 and
m is an integer between 1 and 15.

* * * * *